United States Patent [19]

Rosenbaum

[11] Patent Number: 5,585,386
[45] Date of Patent: Dec. 17, 1996

[54] α-PYRONE COMPOSITIONS FOR INDUCING/STIMULATING HAIR GROWTH AND/OR RETARDING HAIR LOSS

[75] Inventor: Georges Rosenbaum, Paris, France

[73] Assignee: L'Oreal, Paris, France

[21] Appl. No.: 404,575

[22] Filed: Mar. 15, 1995

[30] Foreign Application Priority Data

Mar. 15, 1994 [FR] France ................... 94 02992

[51] Int. Cl.⁶ .................. A61K 31/35; A61K 31/355; A61K 31/44
[52] U.S. Cl. ............ 514/337; 514/458; 514/460
[58] Field of Search ................... 514/460, 465, 514/337, 458

[56] References Cited

U.S. PATENT DOCUMENTS 4,139,619  2/1979  Chidsey ................. 424/45

FOREIGN PATENT DOCUMENTS 3275514  11/1988  Japan.
9308800   5/1993  WIPO.

OTHER PUBLICATIONS

EUR. J. Pharmacol., vol. 215, No. 2–3, 1992, pp. 265–269, C. Backhaus et al., "Extract of kava (Piper methysticum) and its methysticin constituents protect brain tissue against ischemic damage in rodents."

Therapiewoche, vol. 34, No. 27, 1984, pp. 4117–4127, K. Schimmel, "Pflanzliche sedativa."

*Primary Examiner*—Phyllis G. Spivack
*Attorney, Agent, or Firm*—Burns, Doane, Swecker & Mathis, L.L.P.

[57] ABSTRACT

Topically applicable hair growth-/hair loss-affecting cosmetic/therapeutic compositions are disclosed for treating mammalian subjects with hair or scalp disorders comprising an effective amount of at least one α-pyrone compound as kavain, formulated into a physiologically topically acceptable carrier medium, whether organic or aqueous, or mixtures thereof.

29 Claims, No Drawings

α-PYRONE COMPOSITIONS FOR INDUCING/STIMULATING HAIR GROWTH AND/OR RETARDING HAIR LOSS

BACKGROUND OF THE INVENTION

1. Field of the Invention

The present invention relates to novel cosmetic and/or therapeutic compositions for topical application to mammalian subjects, comprising at least one α-pyrone as the active principle thereof, and to the use of such novel compositions for inducing and stimulating hair growth and/or retarding hair loss.

2. Description of the Prior Art

In human subjects hair growth and renewal are principally determined by the activity of the hair follicles. This activity is cyclic and essentially entails three phases, namely, the anagen phase, the catagen phase and the telogen phase.

The active anagen phase, or growth phase, which lasts for several years during which the hair elongates, is succeeded by a very short and transient catagen phase and then a rest or quiescent phase, designated the telogen phase, which lasts for a few months.

At the end of the rest period, the hairs are shed and another cycle begins anew. The head of hair is hence being constantly renewed and, of the approximately 150,000 hairs on a human head, approximately 10% are at rest at any given instant and thus will be replaced in a few months.

In a large number of cases, early hair loss occurs in genetically predisposed subjects, and it affects men in particular. This applies, more especially, to androgenetic or androgenic or, alternatively, androgeno-genetic alopecia.

This alopecia is essentially due to a disturbance of hair renewal, which initially gives rise to an acceleration of the frequency of the cycles at the expense of the quality of the hairs, and then of their quantity. There is a gradual depletion of the head of hair through regression of so-called "terminal" hairs at the down stage. Some regions are affected preferentially, in particular the temporal or frontal areas in men, and a diffuse alopecia of the crown is observed in women.

Compositions that eliminate or reduce the effects of androgenetic alopecia and, in particular, that induce or stimulate hair growth or decrease hair loss have long been considered desiderata in the cosmetic and pharmaceutical industries.

In this regard, a large number of very diverse active compounds have been suggested for such purposes, for example, 6-amino-1,2-dihydro-1-hydroxy-2-imino-4-piperidinopyrimidine and derivatives thereof, as described, more especially, in U.S. Pat. No. 4,139,619. Nonetheless, considerable research and development is continuing in this art in quest of yet other such valuable active agents.

SUMMARY OF THE INVENTION

Accordingly, a major object of the present invention is the provision of compounds of the α-pyrone type for efficaciously inducing/stimulating hair growth and/or decreasing hair loss.

Briefly, the present invention features novel cosmetic and/or therapeutic compositions for inducing and stimulating hair growth and/or retarding hair loss, comprising, in a physiologically acceptable medium, at least one α-pyrone having the following structural formula:

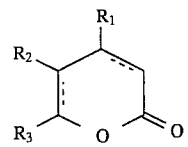

in which $R_1$ is a hydrogen atom or an alkoxy radical having from 1 to 4 carbon atoms; $R_2$ is a hydrogen atom or a hydroxyl group; and $R_3$ is an alkyl radical having from 1 to 4 carbon atoms or a styryl or phenethyl radical optionally substituted by one or two methylenedioxy radicals or one or two hydroxyl groups and/or one or two alkoxy radicals having from 1 to 4 carbon atoms, with the proviso that, when $R_2$ is a hydroxyl group, then $R_3$ is necessarily an unsubstituted phenethyl radical.

DETAILED DESCRIPTION OF BEST MODE AND PREFERRED EMBODIMENTS OF THE INVENTION

More particularly, according to the present invention, it will be appreciated that the α-pyrone(s) comprising the subject compositions contain(s) either single- or one or two double-bonds.

The present invention also features topical application of the subject cosmetic/therapeutic compositions for inducing/stimulating hair growth and/or for preventing/retarding hair loss.

Among the α-pyrone compounds comprising the cosmetic/therapeutic compositions of the invention, preferred are those in which:

(i) $R_1$ and $R_2$ are hydrogen atoms and $R_3$ is a methyl radical, namely, parasorbic acid, also known as parasorbinic acid, or 5,6-dihydro-6-methyl-2H-pyran-2-one;

(ii) $R_1$ and $R_2$ are hydrogen atoms and $R_3$ is a methyl radical, namely, 5-methyl-δ-valerolactone or tetrahydro-6-methyl-2H-pyran-2-one;

(iii) $R_1$ is a methoxy radical, $R_2$ is a hydrogen atom and $R_3$ is a styryl radical, namely, kavain or 5,6-dihydro-4-methoxy-6-(2-phenylethenyl)-2H-pyran-2one;

(iv) $R_1$ is a methoxy radical, $R_2$ is a hydrogen atom and $R_3$ is a styryl radical, namely, 5,6-dehydrokavain or 4-methoxy-6-(2-phenylethenyl)-2H-pyran-2-one;

(v) $R_1$ is a methoxy radical, $R_2$ is a hydrogen atom and $R_3$ is a phenethyl radical, namely, 7,8-dihydrokavain or marindinin or 5,6-dihydro-4-methoxy-6-(2-phenylethyl)-2H-pyran-2-one;

(vi) $R_1$ is a methoxy radical, $R_2$ is a hydroxyl group and $R_3$ is a phenethyl radical, namely, dihydrokavain-5-ol or 5,6-dihydro-5-hydroxy-4-methoxy-6-(2-phenylethyl)-2H-pyran-2-one;

(vii) $R_1$ is a methoxy radical, $R_2$ is a hydrogen atom and $R_3$ is a 3,4-methylenedioxystyryl radical, namely, methysticin or 6-[2-(1,3-benzodioxol-5-yl)ethenyl]-5,6-dihydro-4-methoxy-2H-pyran-2-one;

(viii) $R_1$ is a methoxy radical, $R_2$ is a hydrogen atom and $R_3$ is a 3,4-methylenedioxyphenethyl radical, namely, 7,8-dihydromethysticin or 6-[2-(1,3-benzodioxol-5-yl)ethyl]-5,6-dihydro-4-methoxy-2H-pyran-2-one;

(ix) $R_1$ is a methoxy radical, $R_2$ is a hydrogen atom and $R_3$ is a 4-methoxystyryl radical, namely, yangonin or 4-methoxy-6-[2-methoxyphenyl)ethenyl]-2H-pyran-2-one;

(x) $R_1$ is a methoxy radical, $R_2$ is a hydrogen atom and $R_3$ is a 4-hydroxystyryl radical, namely, noryangonin or 6-[2-(4-hydroxyphenyl)ethenyl]-4-methoxy-2H-pyran-2-one;

(xi) $R_1$ is a methoxy radical, $R_2$ is a hydrogen atom and $R_3$ is a 4-hydroxy-3-methoxystyryl radical, namely, 11-methoxynoryangonin or 6-[2-(4-hydroxy-3-methoxyphenyl)ethenyl]-4-methoxy-2H-pyran-2-one;

(xii) $R_1$ is a methoxy radical, $R_2$ is a hydrogen atom and $R_3$ is a 3,4-dimethoxystyryl radical, namely, 11-methoxyyangonin or 6-[2-(3,4-dimethoxyphenyl)ethenyl]-4-methoxy-2H-pyran-2-one;

(xiii) $R_1$ is a methoxy radical, $R_2$ is a hydrogen atom and $R_3$ is a 4-methoxyphenethyl radical, namely, 7,8-dihydroyangonin or 4-methoxy-6-[2-(4methoxyphenyl)ethyl]-2H-pyran-2-one.

According to the present invention, 5-methyl-δ-valerolactone and kavain are the most preferred compounds.

The α-pyrone compounds having the structural formula given above are preferably employed in proportions ranging from approximately 0.05% to 10% by weight, and more preferably from 0.1% to 6% by weight, relative to the total weight of the composition.

All of these α-pyrone compounds are per se well known to this art.

Kavain and its derivatives, methysticin and its derivatives and yangonin and its derivatives are present in the natural state in the Polynesian plant Piper Methysticum or Kawakawa; parasorbic acid is, in particular, present in Sorbus Aucuparia berries; and 5-methyl-δ-valerolactone is, in particular, present in Avena Sativa. They may be extracted from these various sources via any one of a number of well-known extraction techniques.

These compounds may also be synthesized according to a variety of processes described in the literature.

Thus, kavain and derivatives thereof can be prepared via the processes described in Fowler et al, *J. Chem. Soc.*, 3642 (1950); T. Isawa et al, *Chem. Lett.*, 161 (1975); Z. H. Israili et al, *J. Org. Chem.*, 41, 4070 (1976); S. Castellino et al, *Tetrahedron Lett.*, 25, 4059 (1984); A. Belanger et al, *Can. J. Chem.*, 53, 201 (1975); E. Susuki et al, *Synthesis*, 192 (1975); H. Achenbach et al, *Tetrahedron Lett.*, 3259 (1970) and 119 (1974); R. Haensel et al, *Chem. Ber.*, 106, 570 (1973).

Other of these compounds can be prepared via the processes described in the following publications:

(a) Methysticin and derivatives thereof: M. W. Klohs et al, *J. Org. Chem.*, 24, 1829 (1959);

(b) Yangonin and derivatives thereof: T. M. Harris et al, *J. Org. Chem.*, 33, 2399 (1968); E. Hipolito et al, *Rev. Latinoam. Quim.*, 8, 79 (1977);

(c) Parasorbic acid: L. J. Haynes et al, *J. Chem. Soc.*, 954 (1946); T. Sato, *Heterocycles*, 24, 2173 (1986); R. Stevenson et al, *J. Nat. Prod. (Lloydia)*, 51, 1215 (1988); A. S. Gopalan et al, *Tetrahedron Lett.*, 31, 5575 (1990);

(d) 5-Methyl-δ-valerolactone: T. H. Parliment et al, *Chem. Ind. (London)*, 1845 (1966); D. Taub et al, *Tetrahedron*, 24, 2443 (1968); G. Sturtz et al, *Tetrahedron Lett.*, 47 (1976); D. Seebach et al, *Helv. Chim. Acta*, 698, 2342 (1985); B. Giese et al, *J. Org. Chem.*, 51, 3726 (1986).

The physiologically acceptable medium formulated into the compositions according to the invention can be anhydrous or, to the contrary, aqueous. By "anhydrous medium" is intended a solvent medium containing less than 1% of water. This medium can essentially consist of a solvent or a mixture of solvents selected, more especially, from among $C_2$–$C_4$ lower alcohols such as ethyl alcohol, alkylene glycols such as propylene glycol, and alkylene glycol or dialkylene glycol alkyl ethers in which the alkyl or alkylene radicals have from 1 to 4 carbon atoms. By "aqueous medium" is intended a medium consisting of water or a mixture of water and another physiologically acceptable solvent selected, in particular, from among the organic solvents indicated above. In the latter case, these other solvents, when present, constitute approximately 5% to 95% by weight of the composition.

The subject compositions can contain other adjuvants and additives typically employed in the cosmetic or pharmaceutical arts for the purpose of providing topically applicable compositions, such as surfactants, thickening or gelling agents, cosmetic agents, preservatives and alkalinizing or acidifying agents which are well known to the art, and in amounts sufficient to obtain the desired form of presentation, in particular of a more or less thickened lotion, a gel, an ointment, a salve, an emulsion or a cream. The composition can also, where appropriate, be pressurized as an aerosol or vaporized from a pump bottle.

When the composition is thickened or gelled using a thickening agent, such thickening agent is generally present in concentrations ranging from approximately 0.1% to 6% relative to the total weight of the composition.

The subject compositions can be used, in particular, in treatments employing an application, whether or not followed by a rinse, or, alternatively, in the form of a shampoo.

The pH of the subject compositions advantageously ranges from approximately 3 to 9, and preferably from 5 to 8.

The compositions according to the invention can contain, other than the α-pyrone, compounds which further improve or enhance the activity in respect of hair regrowth and/or in respect of retarding hair loss, and which are already known for such activity.

Exemplary such compounds include:

(a') nicotinic acid esters including, in particular, tocopherol nicotinate, benzyl nicotinate and $C_1$–$C_6$ alkyl nicotinates, such as methyl or hexyl nicotinate;

(b') steroidal and non-steroidal anti-inflammatory agents, especially hydrocortisone, its salts and derivatives thereof, niflumic acid, and the like;

(c') retinoids such as all-trans-retinoic acid, also known as tretinoin, isotretinoin, retinol or vitamin A, and derivatives thereof, for example the acetate, palmitate or propionate, motretinide, etretinate and zinc all-trans-retinoate;

(d') pyrimidine derivatives such as 6-amino-1,2-dihydro-1-hydroxy-2-imino-4-piperidinopyrimidine, also known as "Minoxidil" as described in U.S Pat. No. 4,139,619;

(e') antibacterial agents such as macrolides, pyranosides and tetracyclines, and erythromycin in particular;

(f') calcium antagonists such as cinnarizine and diltiazem;

(g') hormones such as oestriol or analogs thereof or thyroxine and salts thereof;

(h') antiandrogens such as oxendolone, spironolactone and diethylstilbestrol;

(i') 5-δ-reductase inhibitors;

(j') OH radical trapping agents such as dimethyl sulfoxide.

Other such compounds include, for example, diazoxide, spiroxazone, phospholipids such as lecithin, linoleic and linolenic acids, salicylic acid and derivatives thereof described in FR-2,581,542, such as salicylic acid derivatives bearing an alkanoyl substituent having 2 to 12 carbon atoms at position 5 of the benzene ring, hydroxycarboxylic or ketocarboxylic acids and esters thereof, lactones and their corresponding salts, anthralin, carotenoids, and icosatetraynoic and icosatriynoic acids or the esters and amides thereof.

The regime for treating hair loss entails applying an effective amount of a composition according to the invention to the alopecic regions of an individual's scalp and hair, permitting it to remain there for several hours and, where appropriate, in rinsing.

For example, such a composition can be applied to the hair and scalp at night, kept there all night long and, where appropriate, shampooed out in the morning. Alternatively, the hair may be washed using this composition, and maintained in contact with the hair and scalp for a few minutes before rinsing. These applications may be repeated daily for one or several months, depending on the particular individual.

The aforesaid regimes are also in the nature of a cosmetic treatment, inasmuch as they improve the attractiveness of the hair by imparting more bounce and a better appearance thereto.

The α-pyrones described above can also be used in formulations for the treatment of scalp disorders such as alopecia.

In order to further illustrate the present invention and the advantages thereof, the following specific examples are given, it being understood that same are intended only as illustrative and in nowise limitative.

EXAMPLE 1:

A lotion having the following composition for combating hair loss was prepared:

|  |  |  |
|---|---|---|
| (i) | Kavain | 1.0 g |
| (ii) | Propylene glycol | 10.0 g |
| (iii) | Isopropyl alcohol | qs 100.0 g |

1 ml of this lotion is applied to the scalp at the rate of once to twice daily.

EXAMPLE 2:

A lotion having the following composition for combating hair loss was prepared:

|  |  |  |
|---|---|---|
| (i) | 5-Methyl-δ-valerolactone | 1.5 g |
| (ii) | Propylene glycol | 30.0 g |
| (iii) | Ethyl alcohol | 40.5 g |
| (iv) | Water | qs 100.0 g |

This lotion is applied to the scalp once to twice daily on the basis of 1 ml per application.

EXAMPLE 3:

A thickened lotion having the following composition for combating hair loss was prepared:

|  |  |  |
|---|---|---|
| (i) | 5-Methyl-δ-valerolactone | 1.0 g |
| (ii) | Kavain | 2.0 g |
| (iii) | Hydroxypropylcellulose (marketed by Hercules under the trademark Klucel G) | 3.5 g |
| (iv) | Ethyl alcohol | qs 100.0 g |

This thickened lotion is applied to the scalp once to twice daily on the basis of 1 ml per application.

EXAMPLE 4:

A thickened lotion having the following composition for combating hair loss was prepared:

|  |  |  |
|---|---|---|
| (i) | Methysticin | 0.5 g |
| (ii) | Propylene glycol monomethyl ether (marketed under the trademark Dowanol PM by Dow Chemical) | 20.0 g |
| (iii) | Hydroxypropylcellulose (marketed by Hercules under the trademark Klucel G) | 3.0 g |
| (iv) | Ethyl alcohol | 40.0 g |
| (v) | Water | qs 100.0 g |

This thickened lotion is applied to the scalp once to twice daily on the basis of 1 ml per application.

Using each of the compositions described in the above Examples 1 to 4, a diminishing of hair loss and/or a regrowth thereof were observed after several months of treatment and depending on the particular subjects treated.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable hair growth-/hair loss-affecting composition of matter, comprising a hair growth stimulating and/or hair loss retarding effective amount of at least one α-pyrone compound having the structural formula:

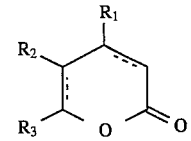

in which $R_1$ is a hydrogen atom or an alkoxy radical having from 1 to 4 carbon atoms, $R_2$ is a hydrogen atom or a hydroxyl group, and $R_3$ is an alkyl radical having from 1 to 4 carbon atoms or a styryl or phenethyl radical optionally substituted by one or two methylenedioxy radicals or one or two hydroxyl groups and/or one or two alkoxy radicals having from 1 to 4 carbon atoms, with the proviso that, when $R_2$ is a hydroxyl group, then $R_3$ is necessarily an unsubstituted phenethyl radical, with the further proviso that when $R_3$ is an alkyl radical having 1 to 4 carbon atoms, then $R_1$ and $R_2$ cannot both be hydrogen, in a physiologically topically acceptable carrier medium.

2. The topical composition as defined by claim 1, wherein said α-pyrone compound is kavain.

3. The topical composition as defined by claim 1, wherein said α-pyrone compound is 5,6-dehydrokavain.

4. The topical composition as defined by claim 1, wherein said α-pyrone compound is 7,8-dihydrokavain.

5. The topical composition as defined by claim 1, wherein said α-pyrone compound is dihydrokavain-5-ol.

6. The topical composition as defined by claim 1, wherein said α-pyrone compound is methysticin.

7. The topical composition as defined by claim 1, wherein said α-pyrone compound is 7,8-dihydromethysticin.

8. The topical composition as defined by claim 1, wherein said α-pyrone compound is yangonin.

9. The topical composition as defined by claim 1, wherein said α-pyrone compound is noryangonin.

10. The topical composition as defined by claim 1, wherein said α-pyrone compound is 11-methoxynoryangonin.

11. The topical composition as defined by claim 1, wherein said α-pyrone compound is 11-methoxyyangonin.

12. The topical composition as defined by claim 1, wherein said α-pyrone compound is 7,8-dihydroyangonin.

13. The topical composition as defined by claim 1, comprising from about 0.05% to about 10% by weight of said at least one α-pyrone compound.

14. The topical composition as defined by claim 13, comprising from about 0.1% to about 6% by weight of said at least one α-pyrone compound.

15. The topical composition as defined by claim 1, said physiologically topically acceptable carrier medium comprising an anhydrous organic solvent medium.

16. The topical composition as defined by claim 15, said anhydrous organic solvent medium comprising a lower alcohol, an alkylene glycol, an alkylene glycol or dialkylene glycol alkyl ether, or mixture thereof.

17. The topical composition as defined by claim 1, said physiologically topically acceptable carrier medium comprising an aqueous medium.

18. The topical composition as defined by claim 17, said aqueous medium also comprising from 5% to 95% by weight of an organic solvent.

19. The topical composition as defined by claim 1, further comprising at least one conventional cosmetic/pharmaceutical additive or adjuvant.

20. The topical composition as defined by claim 19 comprising at least one surfactant, thickening agent, gelling agent, cosmetically active agent, preservative, alkalinizing agent or acidifying agent.

21. The topical composition as defined by claim 19, comprising from about 0.1% to 6% by weight of a thickening agent.

22. The topical composition as defined by claim 1, having a pH ranging from 3 to 9.

23. The topical composition as defined by claim 22, having a pH ranging from 5 to 8.

24. The topical composition as defined by claim 1, further comprising at least one hair growth-/hair loss-affecting active agent wherein said agent is a nicotinic acid ester.

25. The topical composition as defined by claim 1, comprising a lotion, cream, gel, emulsion, ointment, salve, or shampoo.

26. The topical composition as defined by claim 25, comprising an aerosol or spray.

27. A topically applicable hair growth-/hair loss-affecting composition of matter, consisting essentially of a hair growth stimulating and/or hair loss retarding effective amount of at least one α-pyrone compound having the structural formula:

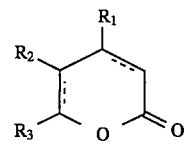

in which $R_1$ is a hydrogen atom or an alkoxy radical having from 1 to 4 carbon atoms, $R_2$ is a hydrogen atom or a hydroxyl group, and $R_3$ is an alkyl radical having from 1 to 4 carbon atoms or a styryl or phenethyl radical optionally substituted by one or two methylenedioxy radicals or one or two hydroxyl groups and/or one or two alkoxy radicals having from 1 to 4 carbon atoms, with the proviso that, when $R_2$ is a hydroxyl group, then $R_3$ is necessarily an unsubstituted phenethyl radical, and with the further proviso that if $R_3$ is an alkyl radical having 1 to 4 carbon atoms, then $R_1$ and $R_2$ cannot both be hydrogen, in a physiologically topically acceptable carrier medium.

28. A method for inducing/stimulating hair growth and/or retarding hair loss on a mammalian subject, comprising topically applying to the hair and/or skin of said mammalian subject an effective amount of the topical composition as defined by claim 1, for a time sufficient to elicit said hair growth-/hair loss-affecting response.

29. The method as defined by claim 28, comprising topically applying said composition to the hair or scalp of said mammalian subject, for the therapeutic treatment of a disorder thereof.

* * * * *